United States Patent [19]

MacLeod

[11] Patent Number: 5,334,606
[45] Date of Patent: Aug. 2, 1994

[54] OXAZOLIDINDIONE SUBSTITUTED INDOLE DERIVATIVES

[75] Inventor: Angus M. MacLeod, Bishops Stortford, England

[73] Assignee: Merck Sharpe & Dohme Ltd., Hoddesdon, England

[21] Appl. No.: 982,794

[22] Filed: Nov. 30, 1992

[30] Foreign Application Priority Data

Dec. 3, 1991 [GB] United Kingdom .............. 9125726.1
Mar. 31, 1992 [GB] United Kingdom .............. 9207055.6
Jul. 30, 1992 [GB] United Kingdom .............. 9216237.9

[51] Int. Cl.⁵ .......................................... C07D 263/40
[52] U.S. Cl. ................................. 514/376; 548/226;
548/183; 548/312.1; 548/518; 548/504;
548/517; 514/369; 514/389; 514/415; 514/421;
514/422
[58] Field of Search ................. 548/226; 514/376

[56] References Cited

U.S. PATENT DOCUMENTS

| | | | |
|---|---|---|---|
| 4,407,811 | 10/1983 | Schnur | 514/376 |
| 4,753,956 | 6/1988 | Schnur | 548/226 |
| 4,968,707 | 11/1990 | Clark et al. | 514/376 |
| 5,143,927 | 9/1992 | Boschelli et al. | 548/226 |
| 5,208,250 | 4/1993 | Cetenko et al. | 548/226 |

FOREIGN PATENT DOCUMENTS

| | | |
|---|---|---|
| 0313397 | 4/1989 | European Pat. Off. . |
| 0343643 | 11/1989 | European Pat. Off. . |
| 0121758 | 10/1978 | Japan .................................. 548/226 |

OTHER PUBLICATIONS

Shepheard et al. Br. Jour. Pharmacol. vol. 108 pp. 11–12 (1993).
Monthly Index of Medical Specialties, Jan. 1994 p. 107.
Burger, "Medicinal Chemistry 2d Ed." Interscience, N.Y. 1960 pp. 42–43.
J. Chem. Soc. (C), 1969, pp. 1855–1858, by N. B. Chapman, et al., entitled "Pharmacologically Active Benzo b thiophen Derivatives".
J. Med. Chem., vol. 24, No. 4, pp. 465–468 (1981), by N. Mehta, et al., entitled Potential Anticonvulsants.¹1. 5-Benzylhydantoins.
J. Indian Chem. Soc., vol. 35, No. 4 (1958), pp. 287–293, by M. Rour, entitled Thiohydantoins and Their Derivatives and Use of Some of Them in the Estimation of Silver, Mercury and Copper.
Angem. Chem., vol. 95, 11, pp. 892–893 (1983).
J. Med. Chem. vol. 33, pp. 1418–1423, by A. Zask, et al., entitled Synthesis & Antihyperglycemic Activity of Novel 5-Naphthalenylsulfonyl)-2,4-thiazolidinediones (1990).
J. Gootjes, et al., Arneimittel Forschung Drug Research, vol. 9, pp. 1145–1149 (1967).

*Primary Examiner*—Donald G. Daus
*Attorney, Agent, or Firm*—Robert J. North; Melvin Winokur

[57] ABSTRACT

Compounds of formula (I):

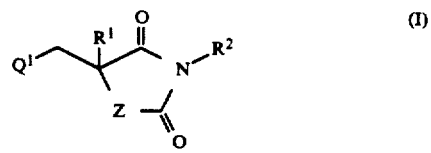

wherein
$Q^1$ represents a phenyl group substituted by one or more halo; naphthyl; indolyl; benzthiophenyl; benzofuranyl; benzyl; or fluorenyl;
$R^1$ is H, $C_{1-6}$alkyl or $C_{2-6}$alkenyl;
$R^2$ is phenyl($C_{1-4}$alkyl) optionally substituted in the phenyl ring by one or more groups selected from $C_{1-6}$alkyl, $C_{2-6}$alkenyl, $C_{2-6}$alkynyl, halo, cyano, nitro, trifluoromethyl, $SR^b$, $SOR^b$, $SO_2R^b$, $OR^b$, $NR^bR^c$, $NR^bCOR^c$, $NR^bCOOR^c$, $COOR^b$ or $CONR^bR^c$, where $R^b$ and $R^c$ independently represent H, $C_{1-6}$alkyl, phenyl or trifluoromethyl; and
Z is O, S, $NR^8$ or $CR^9R^{10}$, where $R^8$ represents H $C_{1-6}$alkyl, phenyl, phenyl($C_{1-4}$alkyl), $COR^{11}$, $COOR^{11}$, $CONR^9R^{10}$ where $R^{11}$ is phenyl, phenyl($C_{1-4}$alkyl) or $C_{1-6}$alkyl, and $R^9$ and $R^{10}$ are each H, $C_{1-6}$alkyl, phenyl or phenyl($C_{1-4}$alkyl); are tachykinin antagonists. They and their compositions are useful in medicine.

5 Claims, No Drawings

OXAZOLIDINDIONE SUBSTITUTED INDOLE DERIVATIVES

This invention relates to a class of heterocyclic compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg—Pro—Lys—Pro—Gln—Gln—Phe—Phe—Gly—Leu—Met—$NH_2$

Neurokinin A:
His—Lys—Thr—Asp—Ser—Phe—Val—Gly—Leu—Met—$NH_2$

Neurokinin B:
Asp—Met—His—Asp—Phe—Phe—Val—Gly—Leu—Met—$NH_2$

Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817–37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], vasodilation, bronchospasm, reflex or neuronal control the viscera [Mantyh et al, PNAS (1988) 85 3235–9] and, possibly by arresting or slowing $\beta$-amyloid-mediated neurodegenerative changes [Yankner et al, Science (1990) 250, 279–82], in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster to be presented at C. I. N. P. XVIIIth Congress, 28th Jun.–2nd Jul., 1992, in press], and in disorders of bladder function such as bladder detrusor hyperreflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythmatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of the known peptide-based tachykinin receptor antagonists discussed above.

J. Indian Chem. Soc., 35, 287–93 (1958) discloses 5-(1-naphthylmethyl)-3-p-tolylhydantoin. No pharmacological activity is attributed to the compound.

Angew. Chem., 95(11), 892–3 (1983) discloses 3-(2-naphthylmethyl)-1-phenylpyrrolidin-2,5-dione. No pharmacological activity is attributed to the compound.

J. Med. Chem., 33(5), 1418–23 (1990) discloses the compound

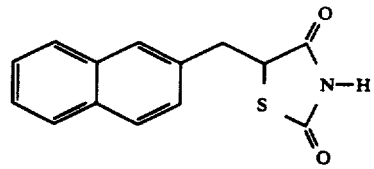

which is said to have antihyperglycaemic activity.

J. Med. Chem., 24(4), 465–8 (1981) discloses the compound

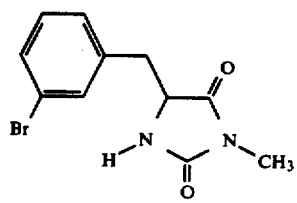

as having weak anticonvulsant activity.

J. Chem. Soc. (C), 1969, 1855–8 discloses 5-(3-benzo[b]thienyl)-5-methylhydantoin. No pharmacological activity is attributed to the compound.

The present invention provides a compound of formula (I), or a salt or prodrug thereof:

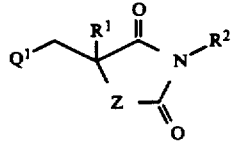

wherein $Q^1$ represents a phenyl group substituted by one or more halo, optionally substituted naphthyl, optionally substituted indolyl, optionally substituted benzthiophenyl, optionally substituted benzofuranyl, optionally substituted benzyl or optionally substituted fluorenyl;

$R^1$ represents H, $C_{1-6}$alkyl or $C_{2-6}$alkenyl;

$R^2$ represents phenyl($C_{1-4}$alkyl) optionally substituted in the phenyl ring by one or more groups selected from $C_{1-6}$alkyl, $C_{2-6}$alkenyl, $C_{2-6}$alkynyl, halo, cyano, nitro, trifluoromethyl, $SR^b$, $SOR^b$, $SO_2R^b$, $OR^b$, $NR^bR^c$, $NR^bCOR^c$, $NR^bCOOR^c$, $COOR^b$ or $CONR^bR^c$, where $R^b$ and $R^c$ independently represent H, $C_{1-6}$alkyl, phenyl or trifluoromethyl; and Z represents O, S, $NR^8$ or $CR^9R^{10}$ where $R^8$ represents H, $C_{1-6}$alkyl, optionally substituted phenyl, optionally substituted phenyl($C_{1-4}$alkyl), $COR^{11}$, $COOR^{11}$, $CONR^9R^{10}$ where $R^{11}$ is optionally substituted phenyl, optionally substituted phenyl($C_{1-4}$alkyl) or $C_{1-6}$alkyl, and $R^9$ and $R^{10}$ each represents H, $C_{1-6}$alkyl, optionally substituted phenyl or optionally substituted phenyl($C_{1-4}$alkyl).

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The alkyl, alkenyl and alkynyl groups referred to with respect to any of the above formulae may represent straight, branched or cyclic groups, or combinations thereof. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkyl-alkyl groups such as cyclopropylmethyl; suitable alkenyl groups include vinyl and allyl; and suitable alkynyl groups include propargyl.

The term "halo" as used herein includes fluoro, chloro, bromo and iodo, especially chloro and fluoro.

Where $R^8$, $R^9$, $R^{10}$ and/or $R^{11}$ are optionally substituted phenyl or optionally substituted phenyl($C_{1-4}$alkyl), suitable phenyl substituents include $C_{1-6}$alkyl, $C_{1-6}$alkoxy, halo and trifluoromethyl.

Where $Q^1$ represents optionally substituted fluorenyl, the group is linked through the bridgehead carbon atom, that is to say, C-9.

Where $Q^1$ represents optionally substituted naphthyl, indolyl, benzthiophenyl, benzofuranyl, benzyl or fluorenyl, suitable substituents include $C_{1-6}$alkyl, $C_{2-6}$alkenyl, $C_{2-6}$alkynyl, halo, cyano, nitro, trifluoromethyl, $SR^b$, $SOR^b$, $SO_2R^b$, $OR^b$, $NR^bR^c$, $NR^bCOR^c$, $NR^bCOOR^c$, $COOR^b$ or $CONR^bR^c$, where $R^b$ and $R^c$ are as above defined. One or more substituents may be present and each may be located at any available ring position, except, where $Q^1$ is optionally substituted indolyl, the nitrogen atom. Where $Q^1$ is optionally substituted indolyl, suitable nitrogen substituents include $C_{1-6}$alkyl, optionally substituted phenyl($C_{1-4}$alkyl), $COOR^b$ or $CONR^bR^c$, wherein $R^b$ and $R^c$ are as above defined.

Suitable values of the group $Q^1$ include 3,4-dichlorophenyl, 3-indolyl, 2-naphthyl, 3-naphthyl, 9-fluorenyl, benzyl, 3-benzthiophenyl and 3-benzofuranyl.

A preferred value of $Q^1$ is 3-indolyl. For example, compounds of formula (I) having this value of $Q^1$ include those of formula (Ia), and salts and prodrugs thereof:

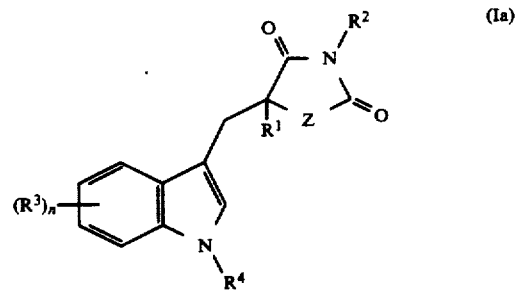

wherein $R^1$, $R^2$ and Z are as defined for formula (I);

each $R^3$ may occupy any available carbon atom of the bicyclic ring system and independently represents $C_{1-6}$alkyl, $C_{2-6}$alkenyl, $C_{2-6}$alkynyl, cyano, nitro, halo, trifluoromethyl, $SR^b$, $SOR^b$, $SO_2R^b$, $OR^b$, $NR^bR^c$, $NR^bCOOR^c$, $COOR^b$ or $CONR^bR^c$, where $R^b$ and $R^c$ are as defined for formula (I);

$R^4$ represents H, $C_{1-6}$alkyl, optionally substituted phenyl($C_{1-4}$alkyl), $COOR^b$ or $CONR^bR^c$, wherein $R^b$ and $R^c$ are as previously defined; and n is 0, 1, 2 or 3.

Suitable values for $R^3$ include methyl, methoxy, chloro, fluoro and trifluoromethyl. Preferably $R^3$ represents methoxy.

When $R^4$ is optionally substituted phenyl($C_{1-4}$alkyl), suitable substituents include $C_{1-6}$alkyl, $C_{1-6}$alkoxy, halo and trifluoromethyl.

Suitably $R^4$ represents H or $C_{1-6}$alkyl, preferably H or methyl.

Suitably, n is 0.

Compounds of formula (I) wherein $Q^1$ is naphthyl include compounds of formula (Ib), and salts and prodrugs thereof:

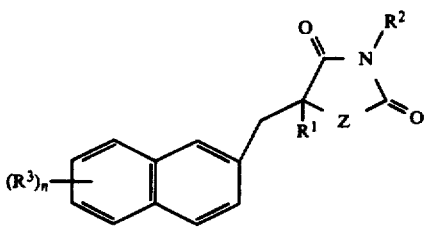

wherein $R^1$, $R^2$, $R^3$, n and Z are as defined for formula (Ia).

Compounds of formula (I) wherein $Q^1$ is 3,4-dichlorophenyl are represented by compounds of formula (Ic), and salts and prodrugs thereof:

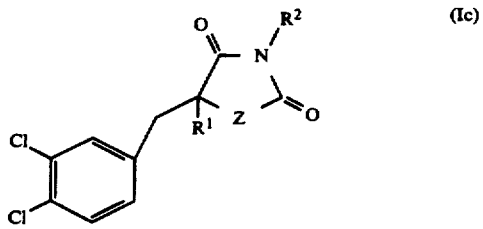

wherein $R^1$, $R^2$ and Z are as previously defined.

A subgroup of compounds of formula (I) is represented by compounds wherein $R^8$ represents H, $C_{1-6}$alkyl, optionally substituted phenyl, optionally substituted phenyl($C_{1-4}$alkyl), $COR^{11}$ or $COOR^{11}$, where $R^{11}$ is optionally substituted phenyl or $C_{1-6}$alkyl.

Within this subgroup may be identified a further subgroup of compounds of formula (I) wherein $R^1$ represents H or $C_{1-6}$alkyl.

With reference to formula (I), preferred values fox the group $R^1$ include H, methyl and 2-propenyl.

Suitably $R^2$ represents benzyl. Preferably $R^2$ represents substituted benzyl, such as disubstituted benzyl. Preferred substituents include methyl, methoxy, chloro, fluoro, cyano, nitro, phenoxy, amino and trifluoromethyl. More preferably $R^2$ represents 3,5-dichlorobenzyl or 3,5-bistrifluoromethylbenzyl.

Where Z represents $NR^8$, suitable values of $R^8$ include H, $C_{1-6}$alkyl, such as methyl, phenyl($C_{1-4}$alkyl), such as benzyl, and $CONR^9R^{10}$ such as $CONHCH_3$ or $CONHC_6H_5$.

Preferably Z represents O or $NR^8$ more preferably O.

A preferred sub-class of compounds according to the invention is represented by compounds of formula (Id), and salts and prodrugs thereof:

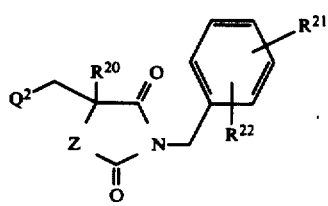

wherein $Q^2$ is optionally substituted indolyl, optionally substituted naphthyl or halo substituted phenyl;

$R^{20}$ represents H, $C_{1-6}$alkyl, preferably $C_{1-4}$alkyl, more preferably methyl, or $C_{2-6}$alkenyl, preferably $C_{2-4}$alkenyl, more preferably propenyl;

$R^{21}$ and $R^{22}$ each independently represent halo or trifluoromethyl; and

Z is O, NH, N-phenyl($C_{1-4}$alkyl), N($C_{1-6}$alkyl), $CONR^9R^{10}$, where $R^9$ and $R^{10}$ are as previously defined, or $CH_2$, more preferably O.

Preferably $R^{21}$ and $R^{22}$ are located in the 3- and 5-positions of the phenyl ring and are the same, preferably chloro or trifluoromethyl.

Particularly preferred are compounds of formula (Id) wherein $Q^2$ is 3-indolyl or N-methyl-3-indolyl, $R^{20}$ is H or methyl, $R^{21}$ and $R^{22}$ each represent trifluoromethyl and Z is O.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

The compounds of the present invention are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example, diabetic and chemotherapy-induced neuropathy, and postherpetic and other neuralgias; respiratory diseases such as chronic obstrucutive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine.

The compounds of formula (I) are particularly useful in the treatment of pain or nociception and/or inflammation and disorders associated therewith such as, for example, neuropathy, such as diabetic or peripheral neuropathy and chemotherapy-induced neuropathy, postherpetic and other neuralgias, asthma, osteroarthritis, rheumatoid arthritis and especially migraine.

The present invention further provides a compound of formula (I) for use in therapy. According to a further or alternative aspect, the present invention provides a compound of formula (I) for use in the manufacture of a medicament for the treatment of a physiological disorder associated with an excess of tachykinins, especially substance P. The present invention also provides a method for the treatment or prevention of a physiological disorder associated with an excess of tachykinins, especially substance P, which method comprises administration to a patient in need thereof of a tachykinin reducing amount of a compound or composition of this invention.

In the treatment of the conditions associated with an excess of tachykinins, a suitable dosage level is about 0.001 to 50 mg/kg per day, in particular about 0.01 to about 25 mg/kg, such as from about 0.05 to about 10 mg/kg per day. For example, in the treatment of conditions involving the neurotransmission of pain sensations, a suitable dosage level is about 0.001 to 25 mg/kg per day, preferably about 0.005 to 10 mg/kg per day, and especially about 0.005 to 5 mg/kg per day. The compounds may be administered on a regimen of 1 to 4 times per day, preferably once or twice per day.

According to one process (A) the compounds of the invention wherein Z is O, S or $NR^8$ may be prepared from intermediates of formula (III):

wherein $R^1$, $R^2$ and $Q^1$ are as defined for formula (I) above and Z is O, S or $NR^8$ by reaction with phosgene or a "phosgene equivalent" such as carbonyl diimidazole, a dialkyl carbonate or an alkylchloroformate.

The reaction may be effected under basic conditions. Suitable bases include, for example, metal alkoxides such as sodium methoxide.

The reaction is conveniently effected in a suitable organic solvent such as an ether, for example, tetrahydrofuran, or a halogenated hydrocarbon, for example, dichloromethane, suitably at room temperature.

According to a second process (B) the compounds according to the invention wherein Z is $CR^9R^{10}$ may be prepared from intermediates of formula (IV)

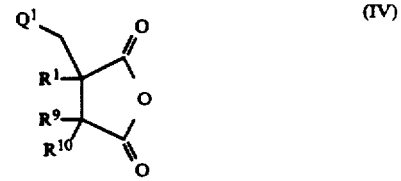

wherein $R^1$, $R^9$, R10 and $Q^1$ are as defined for formula (I), by reaction with a compound of formula $R^2NH_2$ at elevated temperature.

According to an alternative process (C) compounds of the invention wherein Z is O, may be prepared from intermediates of formula (V):

wherein $R^1$ and $Q^1$ are as defined for formula (I), by reaction with carbonyldiimidazole in the presence of a base, followed by a compound of formula $R^2NH_2$.

Suitable bases of use in the reaction include organic bases, such as tertiary amines, for example, triethylamine.

The reaction is conveniently effected in a suitable organic solvent, for example, a halogenated hydrocarbon, for example, dichloromethane, suitably at room temperature.

The above described process (C) constitutes a novel one-pot synthesis of compounds of formula (I).

According to another general process (D) compounds of formula (I) may be prepared from intermediates of formula (VI)

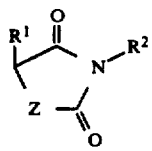

(VI)

where $R^1$, $R^2$ and Z are as defined for formula (I), by reaction with a reagent suitable to introduce the group $Q^1CH_2$, such as, for example, a halide of formula $Q^1CH_2$-Hal, where Hal represent halo such as chloro, bromo or iodo, in the presence of a base.

Suitable bases of use in the reaction include, for example, alkali metal hydrides, such as sodium hydride.

The reaction is conveniently effected in a suitable organic solvent, such as an amide, for example dimethylformamide, or an ether, for example, tetrahydrofuran.

Compounds of formula (I) may also be prepared from other compounds of formula (I) or protected derivatives thereof by interconversion processes. Thus, for example, a compound of formula (I) wherein $R^1$ is $C_{1-6}$alkyl may be prepared from the corresponding compound of formula (I) wherein $R^1$ is H, or a suitably protected derivative thereof, by alkylation, for example, using an alkyl halide.

Intermediates of formula (III) may be prepared from compounds of formula (VII)

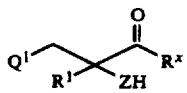

(VII)

wherein $R^1$ and $Q^1$ are as defined for formula (I), Z is as defined for formula (III), and $R^x$ is an alkoxy, halo, hydroxy or $OCOR^y$ group where $R^y$ is alkyl, by reaction with a compound of formula $R^2NH_2$.

Suitable reaction conditions for the amide bond forming reaction will be readily apparent to those skilled in the art. Where $R^x$ represents hydroxy, the reaction is desirably conducted in the presence of a coupling agent, such as dicyclohexylcarbodimide.

The group ZH is suitably protected during the course of the amide bond forming reaction.

Compounds of formula (IV) wherein $R^1$ is H may be prepared from the corresponding compounds of formula (VIII):

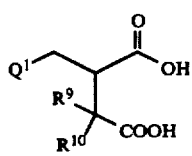

(VIII)

wherein $R^9$, $R^{10}$ and $Q^1$ are as defined for formula (I), by treatment with an anhydride, such as acetic anhydride.

The reaction is suitably conducted at elevated temperature.

Compounds of formula (VIII) may be prepared from compounds of formula (IXA)

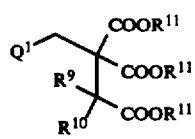

(IX)

wherein $R^9$, $R^{10}$, and $Q^1$ are as defined for formula (I) and $R^{11}$ is H (IXA), by decarboxylation.

Suitable reaction conditions will be readily apparent to those skilled in the art and include heating in the presence of a suitable transition metal, such as copper, and quinoline.

Compounds of formula (IXA) may be prepared from the corresponding compounds of formula (IX) wherein $R^1$ is alkyl (IXB) by treatment with a suitable base followed by protonation.

Suitable bases include alkali metal hydroxides, for example, sodium hydroxide.

Protonation is suitably effected using an appropriate mineral acid, such as hydrochloric acid.

Compounds of formula (IXB) may be prepared by reaction of compounds of formula $Q^1CH_2NR^{12}R^{13}$ wherein $R^{12}$ and $R^{13}$ each represent alkyl, with compounds of formula (X):

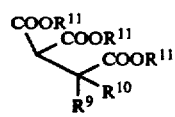

(X)

wherein $R^9$ and $R^{10}$ are as defined for formula (I) and $R^{11}$ is as defined for formula (IXB), in the presence of catalytic sodium.

The reaction is conveniently conducted in a suitable organic solvent, such as a hydrocarbon, for example, toluene.

Compounds of formula (X) wherein $R^9$ and $R^{10}$ are H are commercially available. Compounds of formula (X) wherein $R^9$ and $R^{10}$ are not both H may be prepared by reaction of a compound of formula $CH_2(COOR^{11})_2$ with a compound of formula $R^9R^{10}C(COOR^{11})$Hal, where Hal represents halo, such as chloro or bromo, in the presence of a base. Suitable bases include, for example, metal hydrides, such as sodium hydride.

Compounds of formula (IV) where $R^9$ and $R^{10}$ are H may be prepared from intermediates of formula (XI):

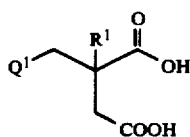

wherein $R^1$ and $Q^1$ are as defined for formula (I) by treatment with an anhydride, such as acetic anhydride.

Compounds of formula (XI) may be prepared from compounds of formula (XII):

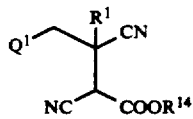

wherein $R^1$ and $Q^1$ are as defined for formula (I) and $R^{14}$ is alkyl, by treatment with an acid, such as a mineral acid, e.g. hydrochloric acid, preferably at elevated temperature.

Compounds of formula (XII) may be prepared from compounds of formula (XIII):

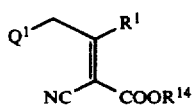

by reaction with an alkali metal cyanide, such as sodium cyanide.

The reaction is conveniently effected in a suitable solvent, such as an aqueous alcohol, e.g. aqueous ethanol, preferably at elevated temperature.

Compounds of formula (XIII) may be prepared from compounds of formula $Q^1CH_2COR^1$ by reaction with a compound of formula $NCCH_2CO_2R^{14}$ in the presence of an acid, such as an organic acid, e.g. acetic acid.

The reaction is conveniently effected in a suitable organic solvent, such as a hydrocarbon, e.g. benzene.

compounds of formula (V) are commercially available or may be prepared by known methods or methods analogous thereto.

Intermediates of formula (VI) wherein Z is O, S or $NR^8$ may be prepared from compounds of formula (XIV)

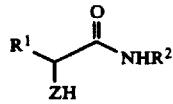

where $R^1$ and $R^2$ are as defined for formula (I) and Z is O, S or $NR^8$ as described for the preparation of compounds of formula (I) from compounds of formula (III).

Compounds of formula (XIV) may be prepared from compounds of formula (XV)

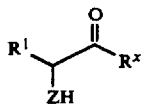

wherein $R^1$, Z and $R^x$ are as defined for formula (VII) above, similarly to the preparation of compounds of formula (III) from compounds of formula (VII).

Compounds of formula (XV) are commercially available or may be prepared from commercially available compounds by conventional procedures well-known to those skilled in the art.

Intermediates of formula (VI) wherein Z is $CR^9R^{10}$ may be prepared from compounds of formula (XVI)

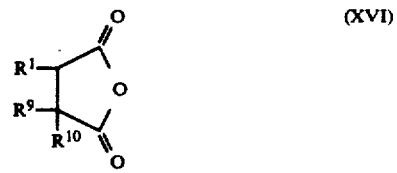

wherein $R^1$, $R^9$ and $R^{10}$ are as defined for formula (I), by reaction with a compound of formula $R^2NH_2$ at elevated temperature.

Where the above-described processes for the preparation of the compounds according to the invention give rise to mixtures of stereoisomers, these isomers may be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following non-limiting Examples illustrate the preparation of compounds according to the invention.

EXAMPLE 1:
3-(3,5-Bistrifluoromethylbenzyl)-5-(indol-3-ylmethylene)oxazolidin-2,4-dione a) Indolelactic acid 3,5-bistrifluoromethylbenzylamide Indolelactic acid (2.0 g) suspended in dichloromethane (25 ml) was treated with triethylamine (2.8 ml) and tertbutyldimethylsilyl triflate (2.3 ml) for 16 hours. Triethylamine (2 ml) was then added followed by isobutylchloroformate (1.5 ml). After stirring for 30 minutes 3,5-bistrifluoromethylbenzylamine (2.5 g) was added and the reaction stirred a further 2 hours. The mixture was washed with 2N hydrochloric acid, aqueous sodium bicarbonate and water, then dried ($Na_2SO_4$) and concentrated. Chromatography on silica gel, eluting with ethyl acetate-petroleum ether (1:3) gave an oil which was treated with tetrabutylammonium fluoride (20 ml of a 1M solution in tetrahydrofuran) for 16 hours. The solution was concentrated, diluted with dichloromethane, washed with water, dried and concentrated. The residue was purified by chromatography (eluting with ethyl acetate-petroleum ether), followed by crystallisation from diethyl ether-petroleum ether to give the title compound as a white crystalline solid, mp 119° C.; found: C, 56.08; H, 3.85; N, 6.43; $C_{20}H_{16}F_6N_2O_2$ requires C, 55.82; H, 3.75; N, 6.51.

b)
3-(3,5-Bistrifluoromethylbenzyl)-5-(indol-3-ylmethylene)oxazolidin-2,4dione

A solution of the product of part (a) (230 mg) in tetrahydrofuran (1 ml) was stirred with carbonyldiimidazole (160 mg) for 1 hour. The reaction mixture was then chromatographed on silica gel eluting with ethyl acetate-petroleum ether (1:3) to give the title compound as a white solid, mp 145°-146° C.; found: C, 55.33; H, 3.29; N, 6.09; $C_{21}H_{14}F_6N_2O_2$ requires C, 55.27; H, 3.09; N, 6.14.

EXAMPLE 2:
3-(3,5-Bistrifluoromethylbenzyl)-5-(indol-3-ylmethylene)imidazolidin-2,4-dione a) L-Tryptophan 3,5-Bistrifluoromethylbenzylamide Hydrochloride To a stirred solution of N-Boc-L-tryptophan (5 g) and 1-hydroxybenzotriazole (2.48 g) in dimethyl formamide (85 ml) was added 1-(3-dimethylaminopropyl)-3-ethyl carbodiimide hydrochloride (3.15 g) at 0° C. After 30 minutes 3,5-bistrifluoromethylbenzylamine (4.43 g) was added and stirring continued for 16 hours at 25° C. The reaction mixture was diluted with dichloromethane and washed with sodium bicarbonate solution, water and dried ($Na_2SO_4$). The solvents were evaporated in vacuo to give a white solid which was dissolved in methanolic hydrogen chloride and allowed to stand for 16 hours. Concentration under reduced pressure afforded the title compound as a solid.

b)
3-(3,5-Bistrifluoromethylbenzyl)-5-(indol-3-ylmethylene) imidazolidin-2,4-dione The product of part (a)(10.0 g) in dichloromethane (50 ml) was treated with triethylamine (5.9 ml) and carbonyl diimidazole (3.5 g). After stirring for 16 hours the mixture was washed with citric acid solution, then aqueous sodium bicarbonate solution, and dried ($MgSO_4$). The solvent was evaporated and the residue purified by chromatography on silica gel eluting with ethyl acetate-petroleum ether (bp 60°-80° C.), 1:1. The product was recrystallised from diethyl ether-petroleum ether to give the title compound (840 mg), mp 151°-153° C.; found: C, 55.69; H, 3.55; N, 9.25; $C_{21}H_{15}F_6N_3O_2$ requires: C, 55.39; H, 3.32; N, 9.23.

EXAMPLE 3:
1-(3,5-Bistrifluoromethylbenzyl)-3-(inidol-3-ylmethylene)pyrrolidin-2,5-dione a) 3,3-Dicarboxy-4-(indol-3-yl)butanoic acid Gramine (17.4 g) and triethyl 1,1,2-ethanetricarboxylate (24.6 g) were suspended in dry toluene. Sodium (0.05 g) was added and the stirred reaction was heated at reflux for six hours. The reaction mixture was cooled, washed with 2N hydrochloric acid (100 ml) and the organic layer was dried ($MgSO_4$) and evaporated. The resulting brown oil was dissolved in ethanol (400 ml) and potassium hydroxide (56 g) was added. The reaction was heated to reflux for six hours, cooled, poured onto ice and acidified to pH1 with 5N hydrochloric acid. The mixture was saturated with sodium sulphate and extracted with ethyl acetate, dried ($Na_2SO_4$), filtered and evaporated. The resulting oil was crystallised from 1,2-dichloroethane (400 ml) to yield the title compound, mp 184°-185° C.; found: C, 55.33; H, 4.67; N, 4.32; $C_{14}H_{13}NO_6$. 0.75($H_2O$) requires C, 55.17; H, 4.80; N, 4.60%.

b) 3-Carboxy-4-(indol-3yl)butanoic acid 3,3-Dicarboxy-4-(indol-3-yl)butanoic acid (10.0 g) was dissolved in freshly distilled quinoline (50 ml) under dry nitrogen and copper powder (1.0 g, 40–80 mesh) was added. The reaction mixture was treated with ultrasound for 0.5 hours and heated to 125° C. for 0.75 hours and 145° C. for 1 hour. The reaction was cooled and poured onto ice, acidified with 5N hydrochloric acid and saturated with sodium sulphate. The mixture was extracted with ethyl acetate (4×100 ml). The combined organic extract was extracted with 5% sodium bicarbonate solution and the combined aqueous extract was poured onto ice, acidified with 5N hydrochloric acid, saturated with sodium sulphate and extracted with ethyl acetate. The combined organic extracts were dried ($MgSO_4$), filtered and evaporated. The resulting oil was taken up into 1,2 dichloroethane and heated and scratched to induce crystallisation. Filtration gave the title compound as white crystals, mp 144°-145° C.; found: C, 62.93; H, 5.48; N 5.62; $C_{13}H_{13}NO_4$ requires C, 63.15; H, 5.30; N, 5.67% c) 3-(indol-3-ylmethylene)succinic anhydride.

The product of part (b) (5.35 g) was dissolved in acetic anhydride (100 ml) and heated to reflux for six hours. The reaction mixture was cooled and the solvent was removed by evaporation under reduced pressure. The residue was azeotroped with xylene and crystallised from dichloromethane and petroleum ether (bp 60°-80° C.) to give the title compound, mp 90°-91° C., found: C, 67.05; H, 4.99, N, 5.95 $C_{13}H_{11}NO_3$. 0.125($H_2O$) requires C, 67.45; H, 4.90; N, 6.05%.

d)
1-(3,5-Bistrifluoromethylbenzyl)-3-(indol-3-ylmethylene)pyrrolidin-2,5-dione

The product of part (c) (1.5 g) and 3,5 bistrifluoromethylbenzylamine (1.9 g) were dissolved in xylene (100 ml) and heated to reflux under Dean Stark conditions for 16 hours. The reaction mixture was cooled and evaporated and the resulting oil was purified by column chromatography using ethyl acetate-petroleum ether (2:3) on silica gel to yield the title compound as a white solid, mp 68°-69° C.; found: C, 58.46; H, 3.77; N, 6.16. $C_{22}H_{16}F_6N_2O_2$ requires C, 58.16; H, 3.55; N, 6.17%

EXAMPLE 4: a) 3-(3,5-Bistrifluoromethylbenzyl)-5-methyl-5-(1-methylindol-3-ylmethylene)oxazolidin-2,4-dione, b) 3-(3,5-bistrifluoromethylbenzyl)-5-methyl-5-(indol-3-ylmethylene)oxazolidin-2,4-dione and c) 3-(3,5-bistrifluoromethylbenzyl)-5-(1-methylindol-3-ylmethylene)oxazolidin-2,4-dione The product of Example 1 (147 mg) in tetrahydrofuran (2 ml) under an atmosphere of nitrogen was treated with sodium hydride (13 mg of an 60% dispersion in oil) and methyl iodide (25 ml). After stirring for 16 hours water was added and extracted with ethyl acetate. The organic solution was dried ($Na_2SO_4$), concentrated, and the residue purified by chromatography on silica gel eluting with ethyl acetate-petroleum ether (1:3) to give title compound a), mp 113°-114° C.; found: C, 56.96; H, 3.72; N, 5.63. $C_{23}H_{18}F_6N_2O_3$ requires C, 57.05; H, 3.75; N, 5.78.

Further elution gave title compound b), mp 158°-159° C.; found: C, 56.32; H, 3.59; N, 5.89. $C_{22}H_{16}F_6N_2O_3$ requires C, 56.18; H, 3.43; N, 5.98.

Further elution gave title compound c); $^1H$ NMR ($CDCl_3$, 250 MHz)3.36(1H, dd), 3.64(3H, s), 4.43(1H, d), 4.50 (1H, d), 5.10(1H, t), 6.88(1H, s), 6.95-7.17 (3H, m), 7.48 (1H, d), 7.60 (2H, s), 7.72 (1H, s); m/e 488 ($CI+,[M+NH_4+]$).

EXAMPLE 5: 3-(3,5-Bistrifluoromethylbenzyl)-5-(5-methoxyindol-3-ylmethylene)oxazolidin-2,4-dione β-[3-(5-Methoxyindolyl)]-DL-lactic acid (M. J. Gortatowski and M. D. Armstrong, J. Org. Chem, 22, 1217, (1957))(0.85 g) in dichloromethane (15 ml) with triethylamine (0.52 g) was treated with carbonyl diimidazole (0.6 g) and stirred at 20° C. for 0.75 hours. 3,5-Bistrifluoromethylbenzylamine (0.91 g) was added and the reaction was stirred for a further 0.75 hours before adding carbonyl diimidazole (0.69 g) and stirring for 16 hours. The product was purified by column chromatography on silica using ethyl acetate-petroleum ether (1:1) to give the title compound, mp 147°-149° C.; found: C, 54.71; H, 3.53; N, 5.77. $C_{22}H_{16}F_6N_2O_4$ requires C, 54.33; H, 3.32; N, 5.76%.

EXAMPLE 6: 3-(2-Propenyl)-3-(3,5-bistrifluoromethylbenzyl)-5-(indol-3-ylmethylene)oxazolidin-2,4-dione To a solution of the title compound of Example 1 (452 mg) in dimethylformamide (30 ml) under nitrogen at −78° C. was added potassium hexamethyldisilazide (4 ml of a 0.5M solution in toluene). After stirring for 5 minutes allyl bromide (0.12 ml) was added and the solution stirred for 30 minutes. Water was then added and the mixture extracted (3x) with diethyl ether. The combined extracts were dried, concentrated and the residue purified by chromatography on silica gel (eluent ethyl acetate petroleum ether 1:4) to give the title compound as a crystalline solid, mp 124° C. (diethyl ether-petroleum ether); found: C, 58.18; H, 3.83; N, 5.51. $C_{24}H_{18}F_6N_2O_3$ requires C, 58.07; H, 3.65; N, 5.64.

EXAMPLE 7: 3-(3,5-Dichlorobenzyl)-5-(indol-3-ylmethylene)oxazolidin-2,4-dione To a solution of indole lactic acid (0.5 g) in $CH_2Cl_2$ (10 ml) and triethylamine (0.68 ml) was added carbonyldiimidazole (0.78 g). After stirring 1 hour 3,5-dichlorobenzylamine (0.55 g) was added and the solution stirred a further 1 hour. The mixture was eluted through a column of silica gel with ethyl acetate-petroleum ether (1:3) to give the title compound as a crystalline solid, mp 157°-158° C. (ethyl acetate-petroleum ether); found C, 58.80; H, 3.82; N, 7.14. $C_{19}H_{14}Cl_2N_2O_3$ requires C, 58.63; H, 3.63; N, 7.20.

EXAMPLE 8:(−)3-(3,5-Bistrifluoromethylbenzyl)-5-(indol-3-ylmethylene)oxazolindin-2,4-dione Potassium glycidate prepared form D-serine by the method of M. Larcheveque and Y. Petit (Bull. Chim. Soc. Fr, (1989), 130) was dissolved in water which was adjusted to pH2 with concentrated hydrochloric acid. The solution was extracted with diethyl ether (5x) and the combined extracts dried and concentrated to give a colourless liquid.

To a mixture of this liquid (1.0 g) and indole (1.35 g) in $CCl_4$ (25 ml) was added tin tetrachloride (2.1 ml) with stirring at 0° C. After 30 minutes the mixture was diluted with ethyl acetate and 2N sodium hydroxide. The organic solution was separated and the aqueous phase extracted (2x) with ethyl acetate. The aqueous solution was adjusted to pH2 with 5N hydrochloric acid and extracted with ethyl acetate which was then dried and evaporated in vacuo. The residual crude L-indole lactic acid (170 mg) was treated with 3,5-bistrifluoromethylbenzylamine by the method of Example 5 to give the title compound which was obtained as white crystals after chromatography on silica gel (eluent ethyl acetate-petroleum ether 1:3) and crystallisation from diethyl ether-petroleum ether, mp 170° C., $[\alpha]_D^{20} - 58.5$ (C=1, $CH_2Cl_2$); found: C, 55.22; H, 3.32; N, 5.84, $C_{21}H_{14}F_6N_2O_3$ requires C, 55.27; H, 3.09; N, 6.14.

EXAMPLE 9: 5-Methyl-5-(2-naphthylmethyl)-3-(3,5-bistrifluoromethylbenzyl)oxazolidin-2,4-dione a) L-(+)-Lactic Acid 3,5-bistrifluoromethylbenzyl amide 1-(3-Dimethylaminopropyl)-3-ethylcarbodiimide hydrochloride (2.5 g) was added to a solution of L-(+)-lactic acid (1.17 g) and 1-hydroxybenzotriazole (1.99 g) in dimethyl formamide (15 ml) at 0° C. under a nitrogen atmosphere. After stirring for 30 mins, 3,5-bistrifluoromethylbenzylamine was added and the solution was stirred at room temperature for 16h. The solution was diluted with dichloromethane (150 ml) and washed with sodium bicarbonate solution, water and brine. After drying ($Na_2SO_4$) the solvent was evaporated in vacuo to leave a viscous yellow oil.

b) 5-Methyl-3-(3,5-Bistrifluoromethylbenzyl)oxazolidin-2,4-dione

A solution of the product of part (a) (2.3 g), N-methylmorpholine (1 ml) and 1,1-carbonyldiimidazole (1.89 g) in dichloromethane (50 ml) was stirred at room temperature for 16h under a nitrogen atmosphere. The solvent was removed and the residue chromatographed on silica gel (eluent ethyl acetate-petroleum ether 1:1) to five the title compound as a colourless oil (1.41 g).

c)
5-Methyl-5-(2-naphthylmethyl)-3-(3,5-bistrifluoromethylbenzyl)oxazolidin-1,4-dione Sodium hydride (60 mg of a 60% dispersion in oil) was added to a solution of 5-methyl-3-(3,5-bistrifluoromethyl benzyl)oxazolidine-2,4-dione (0.5 g) in dimethyl formamide (10 ml) at room temperature under a nitrogen atmosphere. After stirring for 5 minutes 2-bromomethylnaphthalene (0.33 g) in dimethyl formamide (5 ml) was added and the solution was stirred for 5 hours. Dichloromethane (150 ml) was added and the solution was washed with water. After drying (Na$_2$SO$_4$), the solvent was evaporated and the residue chromatographed on silica gel (eluent ethyl acetate-petroleum ether 1:4) to give the title compound after recrystallisation from diethyl ether, mp 95°-97° C.; found C, 59.96; H, 3.44; N, 2.94. C$_{24}$H$_{17}$F$_6$NO$_3$ requires C, 59.88; H, 3.56; N, 2.91.

EXAMPLE 10:
5-Methyl-5(3,4-dichlorobenzyl)-3-(3,5-bistrifluoromethylbenzyl)oxazolidin-2,4-dione The title compound was prepared by the method of Example 9c) using 3,4-dichlorobenzyl bromide, and crystallised from diethyl ether-petroleum ether, mp 80°-82° C.; found C, 48.10; H, 2.54; N, 2.84. C$_{20}$H$_{13}$Cl$_2$F$_6$NO$_3$ requires C, 48.02; H, 2.62; N, 2.80.

EXAMPLE 11:
1-Benzyl-3-(3,5-bistrifluoromethylbenzyl)-5(indol-3-ylmethylene)imidazolidine-2,4-dione A solution of the compound of Example 2 (0.5 g) in dry tetrahydrofuran (20 ml) was cooled to −78° C. and n-butyl lithium (0.72 ml of a 1.6M solution in hexanes) was added with stirring. After 15 minutes benzyl bromide (0.14 ml) was added. The solution was allowed to warm to room temperature then heated to reflux for 3 hours, cooled and poured into saturated ammonium chloride solution (20 ml). This mixture was extracted with ethyl acetate and the organic layers dried (MgSO$_4$). The residue was purified by chromatography on silica gel eluting with ethyl acetate-petroleum ether (1:3) to give the title compound, mp 154°-156° C.; found: C, 61.66; H, 4.05; N, 7.64; C$_{28}$H$_{21}$F$_6$N$_3$O$_2$ requires: C, 61.65; H, 3.88; N, 7.70.

EXAMPLE 12:
1-Methyl-3-(3,5-bistrifluoromethylbenzyl)-5-(indol-3-ylmethylene)imidazolidine-2,4-dione Prepared by the method of Example 11 using methyl iodide in place of benzyl bromide, mp 145°-147° C.; found: C, 56.54; H, 3.83; N, 8.84; C$_{22}$H$_{17}$F$_6$N$_3$O$_2$ requires: C, 56.30; H, 3.65; N, 8.95.

EXAMPLE 13:
1-Phenylcarboxamide-3-(3,5-bistrifluoromethylbenzyl)-5-(indol-3-ylmethylene)imidazolidine-2,4-dione A solution of the imidazolidinedione from Example 2 (0.5 g) in dry dichloromethane (20 ml) was cooled to −78° C. and n-butyl lithium (0.72 ml of a 1.6M solution in hexanes) was added with stirring. After 15 minutes phenyl isocyanate (0.12 ml) was added. The solution was allowed to warm to room temperature and stirred for a further hour. Water (20 ml) was added and the organic layer separated, dried (MgSO$_4$) and the solvents removed in vacuo. The residue was purified by chromatography on silica gel eluting with ethyl acetate-petroleum ether (1:3) and the product recrystallised from diethyl ether/petroleum ether to give the title compound, mp 170°-172° C.; found: C, 58.80; H, 3.61; N, 9.72; C$_{28}$H$_{22}$F$_6$N$_4$O$_3$ requires: C, 58.54; H, 3.51; N, 9.75.

EXAMPLE 14: 1-Methylcarboxamido-3-(3,5-bistrifluoromethylbenzyl)-5-(indol-3-ylmethylene)imidazolidine-2,4-dione Prepared according to the method of Example 13 using methyl isocyanate, mp 173°-175° C.; found: C, 54.53; H, 3.70; N, 10.95; C$_{23}$H$_{18}$F$_6$N$_4$O$_3$. 0.25Et$_2$O requires: C, 54.29; H, 3.89; N, 10.55.

The following examples illustrate pharmaceutical compositions according to the invention.

EXAMPLE 15A
Tablets containing 1-25 mg of compound

|  | Amount mg | | |
|---|---|---|---|
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 15B
Tablets containing 26-100 mg of compound

|  | Amount mg | | |
|---|---|---|---|
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 16
Parenteral injection

|  | Amount mg |
|---|---|
| Compound of formula (I) | 1 to 100 mg |
| Citric Acid Monohydrate | 0.75 mg |
| Sodium Phosphate | 4.5 mg |
| Sodium Chloride | 9 mg |
| Water for Injections | to 1 ml |

The sodium phosphate, citric acid monohydrate and sodium chloride are dissolved in a portion of the water. The compound of formula (I) is dissolved or suspended in the solution and made up to volume.

EXAMPLE 17
Topical formulation

|  | Amount mg |
|---|---|
| Compound of formula (I) | 1-10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1- receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 μg of the plasmid DNA into 10 million COS cells was achieved by electropotation in 800 μl of transfection buffer (135 mM NaCl, 1.2 mM CaCl$_2$, 1.2 mM MgCl$_2$, 2.4 mM K$_2$HPO$_4$, 0.6 mM KH$_2$PO$_4$, 10 mM glucose, 10 mM N-2-hydroxyethyl-piperazine-N'-2-ethane sulphonic acid (HEPES) pH 7.4) at 260 V and 950 μF using the IBI GENEZAPPER (trademark IBI, New Haven, Conn., USA). The cells were incubated in 10% fetal calf serum, 2 mM glutamine, 100U/ml penicillin-streptomycin, and 90% DMEM media (GIBCO, Grand Island, N.Y., USA) in 5% CO$_2$ at 37° C. for three days before the binding assay.

B. Stable Expression in Chinese Hamster Ovarian Cell Line (CHO)

To establish a stable cell line expressing cloned human NK1R, the cDNA was subcloned into the vector pRcCMV (INVITROGEN). Transfection of 20 μg of the plasmid DNA into CHO cells was achieved by electroporation in 800 μl of transfection buffer supplemented with 0.625 mg/ml Herring sperm DNA at 300 V and 950 μF using the IBI GENEZAPPER (IBI). The transfected cells were incubated in CHO media [10% fetal calf serum, 100 U/ml penicillin-streptomycin, 2 mM glutamine, 1/500 hypoxanthinethymidine (ATCC), 90% IMDM media (JRH BIOSCIENCES, Lenexa, Kans., USA), 0.7 mg/ml G418 (GIBCO)] in 5% CO$_2$ at 37° C. until colonies were visible. Each colony was separated and propagated. The cell clone with the highest number of human NK1R was selected.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM MnCl$_2$, 150 mM NaCl, 0.04 mg/ml bacitracin, 0.004 mg/ml leupeptin, 0.2 mg/ml BSA, 0.01 mM phosphoramidon) such that 200 μl of the cell suspension would give rise to about 10,000 cpm of specific $^{125}$I-SP binding (approximately 50,000 to 200,000 cells). In the binding assay, 200 μl of cells were added to a tube containing 20 μl of 1.5 to 2.5 nM of $^{125}$I-SP and 20 μl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, MD) which was pre-wetted with 0.1% polyethylenimine. The filter was washed with 3 ml of wash buffer (50 mM Tris pH 7.5, 5 mM MnCl$_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of IP$_3$. CHO cells are seeded in 12-well plate at 250,000 cells per well. After incubating in CHO media for 4 days, cells are loaded with 5 μCi of $^3$H-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3 nM to activate the human NK1R. After 30 min of incubation at 37° C., the medium is removed and 0.1 N HCl is added. Each well is sonicated at 4° C. and extracted with CHCl$_3$/methanol (1:1). The aqueous phase is applied to a 1 ml Dowex AG 1X8 ion exchange column. The column is washed with 0.1 N formic acid followed by 0.025 M ammonium formate-0.1 N formic acid. The inositol monophosphate is eluted with 0.2 M ammonium formate-0.1 N formic acid and quantitated by beta counter.

The data in Table 1 were obtained for compounds of formula (I):

TABLE 1

| SUBSTANCE P ANTAGONISM RESULTS | |
|---|---|
| Compound of Ex # | IC$_{50}$ @ NK1R (nM) |
| 1 | 21 |
| 2 | 400 |
| 3 | 250 |
| 4a | 14 |
| 4b | 140 |
| 4c | 300 |
| 5 | 300 |
| 6 | 50 |
| 7 | 200 |
| 8 | 17 |
| 9 | >1000 |
| 10 | 100 |
| 11 | 630 |
| 12 | 160 |
| 13 | 410 |
| 14 | 85 |

We claim:

1. A compound of formula (I):

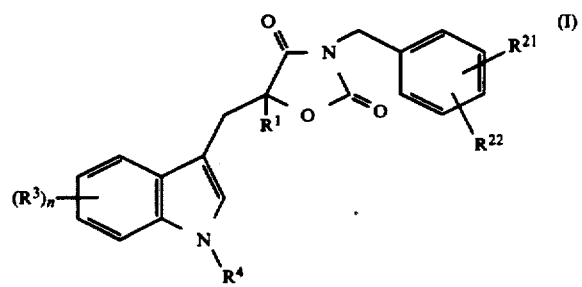

wherein:

R$^1$ is selected from H, C$_{1-6}$alkyl or C$_{2-6}$alkenyl;

each $R^3$ is selected from methyl, methoxy, chloro, fluoro or trifluoromethyl;

$R^4$ is selected from H, $C_{1-6}$alkyl, phenyl ($C_{1-4}$alkyl) optionally substituted by; $C_{1-6}$alkyl, $C_{1-6}$alkoxy, halo or trifluoromethyl; $COOR^b$ or $CONR^bR^c$, wherein $R^b$ and $R^c$ are independently selected from H, $C_{1-6}$alkyl, phenyl or trifluoromethyl;

$R^{21}$ and $R^{22}$ each independently represent halo or trifluoromethyl;

n is 0, 1, 2 or 3;

or a pharmaceutically acceptable salt thereof.

2. A compound as claimed in claim 1 selected from:
3-(3,5-bistrifluoromethylbenzyl)-5-(indol-3-ylmethylene)oxazolidin-2,4-dione;
3-(3,5-bistrifluoromethylbenzyl)-5-(1-methylindol-3-ylmethylene)-oxazolidin-2,4-dione;
3-(3,5-bistrifluoromethylbenzyl)-5-methyl-5-(indol-3-ylmethylene)oxazolidin-2,4-dione;
3-(3,5-bistrifluoromethylbenzyl)-5-(1-methylindol-3-ylmethylene)oxazolidin-2,4-dione;
3-(3,5-bistrifluoromethylbenzyl)-5-(5-methoxyindol-3-ylmethylene)oxazolidin-2,4-dione;
3-(2-propenyl)-3,-(3,5-bistrifluoromethylbenzyl)-5-(indol-3-ylmethylene)-oxazolidin-2,4-dione;
3-(3,5-dichlorobenzyl)-5-(indol-3-ylmethylene)oxazolidin-2,4-dione;
(−)3-(3,5-bistrifluoromethylbenzyl)-5-(indol-3-ylmethylene)oxazolidin-2,4-dione;
or pharmaceutically acceptable salts thereof.

3. A pharmaceutical composition comprising a therapeutically effective amount of a compound according to claim 1 in association with a pharmaceutically acceptable carrier therefor.

4. A method according to claim 1 for the treatment of pain or inflammation.

5. A method according to claim 1 for the treatment of migraine.

* * * * *

UNITED STATES PATENT AND TRADEMARK OFFICE
CERTIFICATE OF CORRECTION

PATENT NO. : 5,334,606

DATED : August 2, 1994

INVENTOR(S) : Angus M. MacLeod

It is certified that error appears in the above-identified patent and that said Letters Patent is hereby corrected as shown below:

At Column 21, in claim 1, please replace line 4, which reads "optionally substituted by;" with -- optionally substituted by: --.

At Column 21, in claim 2, please replace line 4, which reads
"3-(3,5-bistrifluoromethylbenzyl)-5-(1-methylindol-3-", with --
3-(3,5-bistrifluoromethylbenzyl)-5-methyl-5-(1-methylindol-3- --.

At Column 22, in claim 2, please replace line 5, which reads "3-(2-propenyl)-3,-", with -- 3-(2-propenyl)-3- --.

Signed and Sealed this

Sixteenth Day of May, 1995

Attest:

BRUCE LEHMAN

Attesting Officer

Commissioner of Patents and Trademarks